(12) United States Patent
Alleyne et al.

(10) Patent No.: US 8,127,770 B2
(45) Date of Patent: Mar. 6, 2012

(54) METHOD OF USING AN IMPLANT FOR TREAMENT OF LIGAMENTS AND TENDONS

(75) Inventors: Neville Alleyne, La Jolla, CA (US); Stuart Young, Del Mar, CA (US)

(73) Assignee: SpineOvations, Inc., San Diego, CA (US)

( * ) Notice: Subject to any disclaimer, the term of this patent is extended or adjusted under 35 U.S.C. 154(b) by 794 days.

(21) Appl. No.: 11/215,300

(22) Filed: Aug. 30, 2005

(65) Prior Publication Data
US 2006/0074423 A1 Apr. 6, 2006

Related U.S. Application Data

(60) Provisional application No. 60/605,582, filed on Aug. 30, 2004.

(51) Int. Cl.
*A61B 19/00* (2006.01)
*A61F 2/08* (2006.01)
*A61F 2/02* (2006.01)
*A61F 2/00* (2006.01)

(52) U.S. Cl. .................. 128/898; 623/13.11; 623/13.18; 623/23.72; 623/23.73; 623/23.74; 623/23.75; 623/23.76; 424/423

(58) Field of Classification Search ............... 623/23.58, 623/11.11–13.18; 424/423
See application file for complete search history.

(56) References Cited

U.S. PATENT DOCUMENTS

| | | | |
|---|---|---|---|
| 4,526,909 A | 7/1985 | Urist | |
| 4,837,285 A * | 6/1989 | Berg et al. | 530/356 |
| 5,024,659 A | 6/1991 | Sjostrom | |
| 5,171,279 A | 12/1992 | Mathews | |
| 5,258,028 A * | 11/1993 | Ersek et al. | 623/23.73 |
| 5,286,763 A | 2/1994 | Gerhart et al. | |
| 5,290,271 A * | 3/1994 | Jernberg | 604/891.1 |
| 5,344,452 A * | 9/1994 | Lemperle | 623/23.73 |
| 5,352,715 A | 10/1994 | Wallace et al. | |
| 5,571,182 A | 11/1996 | Ersek et al. | |
| 5,599,852 A * | 2/1997 | Scopelianos et al. | 523/105 |
| 5,641,514 A | 6/1997 | Cho | |
| 5,922,025 A | 7/1999 | Hubbard | |
| 6,129,761 A * | 10/2000 | Hubbell | 623/23.72 |
| 6,160,033 A | 12/2000 | Nies | |
| 6,183,518 B1 | 2/2001 | Ross et al. | |
| 6,264,659 B1 * | 7/2001 | Ross et al. | 606/93 |
| 6,264,695 B1 | 7/2001 | Stoy | |
| 6,284,872 B1 * | 9/2001 | Celeste et al. | 530/399 |
| 6,309,420 B1 | 10/2001 | Preissman | |
| 6,335,028 B1 | 1/2002 | Vogel et al. | |
| 6,355,705 B1 | 3/2002 | Bond et al. | |
| 6,391,059 B1 | 5/2002 | Lemperle et al. | |
| 6,432,437 B1 * | 8/2002 | Hubbard | 424/424 |
| 6,468,274 B1 * | 10/2002 | Alleyne et al. | 606/41 |
| 6,652,883 B2 * | 11/2003 | Goupil et al. | 424/489 |
| 6,713,527 B2 | 3/2004 | Bond et al. | |
| 7,060,103 B2 | 6/2006 | Carr et al. | |
| 7,131,997 B2 * | 11/2006 | Bourne et al. | 623/23.72 |
| 7,306,627 B2 | 12/2007 | Tanagho et al. | |
| 7,341,601 B2 | 3/2008 | Eiserman et al. | |
| 2002/0045942 A1 | 4/2002 | Ham | |
| 2002/0176893 A1 * | 11/2002 | Wironen et al. | 424/489 |
| 2003/0009235 A1 | 1/2003 | Manrique et al. | |
| 2003/0149490 A1 | 8/2003 | Ashman | |
| 2003/0158607 A1 | 8/2003 | Carr et al. | |
| 2003/0211083 A1 * | 11/2003 | Vogel et al. | 424/93.7 |
| 2003/0236573 A1 * | 12/2003 | Evans et al. | 623/23.58 |
| 2004/0024465 A1 | 2/2004 | Lambrecht et al. | |
| 2004/0054414 A1 | 3/2004 | Trieu et al. | |
| 2005/0031666 A1 | 2/2005 | Trieu | |
| 2005/0100510 A1 | 5/2005 | Falco | |
| 2006/0002971 A1 | 1/2006 | Saltzman et al. | |
| 2006/0093644 A1 * | 5/2006 | Quelle et al. | 424/423 |
| 2006/0206116 A1 | 9/2006 | Yeung | |
| 2008/0124371 A1 | 5/2008 | Turos et al. | |

FOREIGN PATENT DOCUMENTS

| | | |
|---|---|---|
| EP | 1410810 | 4/2004 |
| EP | 1410810 A1 | 4/2004 |
| WO | WO 98/40113 | 9/1998 |
| WO | WO 00/44808 | 8/2000 |
| WO | WO 0044394 | 8/2000 |
| WO | WO 0044394 A1 * | 8/2000 |
| WO | WO 02/04007 A2 | 5/2002 |
| WO | WO 02/062404 | 8/2002 |
| WO | WO 2008/005676 | 1/2008 |

OTHER PUBLICATIONS

Faught, W.E. and Lawrence, P.F. "The effects of laser energy on the arterial wall." Annals of Vascular Surgery 4 (1990): 198-207.*
Artecoll Product History. Downloaded from <www.artecoll.com> on Jun. 2, 2010.*
International Report on Patentability dated Mar. 8, 2007.
Bayston, et al., "The sustained release of antimicrobial drugs from bone cement. An appraisal of laboratory investigations and their significance," *J. Bone Joint Surg. (Br)*, (1982) 64(4):460-464.
Carruthers, Artecolle®—an injectable micro-implant for longlasting soft tissue augmentation, Skin Therapy Letter, (1999), vol. 4(2), 1-2.
Cohen et al., Artecoll—A Long-Lasting Injectable Wrinkle Filler Material: Report of a Controlled, Randomized, Multicenter Clinical Trial of 251 Subjects, Plastic Reconst. Surg., (2004) vol. 114(4), 964-976.
Wahlig, et al., "Pharmacokinetic study of gentamicin-loaded cement in total hip replacements. Comparative effects of varying dosage," *J. Bone Joint Surg. (Br)*, (1984) 66(2):175-179.

* cited by examiner

*Primary Examiner* — David Isabella
*Assistant Examiner* — Andrew Iwamaye
(74) *Attorney, Agent, or Firm* — Knobbe Martens Olson & Bear LLP

(57) ABSTRACT

A method of treating a ligament or tendon according to the present invention can include inserting a tissue-generating implant into the ligament or tendon to thereby treat the defect. The tissue-generating implant has a plurality of microparticles. The microparticles subsequently form a biological scaffold which operates at least as partial connective tissue in the ligament or tendon giving structural support during regrowth.

11 Claims, No Drawings

US 8,127,770 B2

METHOD OF USING AN IMPLANT FOR TREAMENT OF LIGAMENTS AND TENDONS

CROSS REFERENCE TO RELATED APPLICATIONS

This application claims priority under 35 U.S.C. Section 119(e) to U.S. Provisional Application 60/605,582 filed on Aug. 30, 2004. The entire content of this provisional application is hereby incorporated by reference into this application.

BACKGROUND OF THE INVENTION

1. Field of the Invention

The present invention relates generally to surgical implants and, more particularly, relates to surgical implants and procedures for repairing ligaments and tendons.

2. Description of the Related Art

Ligaments and tendons provide support and stability to the musculoskeletal system. Generally consisting of bands or sheets of fibrous connective tissue, ligaments and tendons when damaged can be painful and often times debilitating. Treatments of these connective tissues can comprise repair by means such as suturing, or can comprise complete or partial replacement with other biological or synthetic materials. As a result of the complexity and functionality of these tissues and general repair considerations, it is generally preferred that the treatment retain and return these tissues to their pre-damaged conditions.

Regarding the repair of ligaments and tendons, as distinguished from replacement, one of the more common ligament repair procedures involves reconstruction of the anterior cruciate ligament (ACL). Several hundred thousand ACL repairs and reconstructions are performed every year in the United States. That number continues to grow as the population continues to become more active in recreational sports and competitive sports such as soccer, football, basketball, track and field. A segment of the population comprises individuals who will end up sustaining partial injuries to their ACL or posterior cruciate ligaments (PCL), requiring surgery to assist in the healing. It has been known for some time that ACL deficient knees and PCL deficient knees can subsequently lead to other intraarticular pathologies, such as meniscal tears or collateral ligament attenuations. Consequently, as with injuries to other ligaments and tendons, the pursuit of effective interventions for efficiently treating injured ligaments and tendons continues to be an active and needed field of active endeavor.

SUMMARY OF THE INVENTION

The present invention introduces implants into ligaments and tendons for repairing or otherwise treating the ligaments or tendons.

In one embodiment, a method of treating a ligament or tendon comprises delivering an implant comprising a plurality of microparticles onto or into the ligament or tendon.

In another embodiment, a medical kit comprises an implant comprising microparticles, and one or more surgical tools configured for repairing at least one tendon or ligament.

In another embodiment, an implant comprising a plurality of microparticles, for use in repairing damaged ligaments or tendons.

In another embodiment, a method of treating a tendon or ligament comprising placing a plurality of particles into contact with at least a portion of the ligament or tendon.

In each of these embodiments, the particles may be suspended in a medium comprising collagen.

DETAILED DESCRIPTION OF THE INVENTION

Any feature or combination of features described herein are included within the scope of the present invention provided that the features included in any such combination are not mutually inconsistent as will be apparent from the context, this description, and the knowledge of one skilled in the art. In addition, any feature or combination of features may be specifically excluded from any embodiment of the present invention. For purposes of summarizing the present invention, certain aspects, advantages and novel features of the present invention are described herein. Of course, it is to be understood that not necessarily all such aspects, advantages or features will be embodied in any particular embodiment of the present invention.

In reference to the disclosure herein, for purposes of convenience and clarity only, directional terms, such as top, bottom, left, right, up, down, upper, lower, over, above, below, beneath, rear, and front, may be used. Such directional terms should not be construed to limit the scope of the invention in any manner. It is to be understood that embodiments presented herein are by way of example and not by way of limitation. The intent of the following detailed description, although discussing exemplary embodiments, is to be construed to cover all modifications, alternatives, and equivalents of the embodiments as may fall within the spirit and scope of the invention.

The present invention provides compositions and methods for selectively treating defects or other conditions within or on ligaments and tendons. These procedures of the present invention primarily relate to ligament and tendon surgeries, such as procedures on flexor or extensor tendons in for example the hand or antebrachium or brachium as well as shoulder, including but not limited to rotator cuff (supraspinatus, infraspinatus, teres minor and subscapularis) but also including biceps tendon, intraarticular and extraarticular, as well as the carpal ligaments in the wrist and at the distal radial ulnar joint and proximal radial ulnar joint. Also included are procedures on ligaments or tendons in and around the pelvis including the sacroiliac joint as well as the insertion at the anterior superior iliac spine of the sartorius, tensor fascia lata or at the anterior inferior iliac spine for the insertion of the rectus, or disruption of the symphysis pubis or at the ischium or the insertion of the biceps femoris and semitendinosus, semimembranosus or the adductor magnus. Moving distally, ligament and tendon repair or augmentation procedures around the hip can include procedures on attachments to the greater trochanter (piriformis, gluteus minimus, gluteus medius, gluteus maximus, obturator internus and the superior and inferior gemelli as well as the obturator externus). As for the lesser trochanter, procedures can be implemented on attachments including psoas major and adductor magnus iliacus. Moving more distally to the distal end of the femur on the medial epicondyle and supracondylar region, procedures can be implemented on attachments including the attachment of the gastroc and the tendon of the adductor magnus. On the lateral condyle, procedures can be implemented on attachments including the plantaris, lateral head of the gastrocnemius popliteus as well as the quadriceps muscle including rectus, vastus medialis, vastus intermedius, vastus lateralis and the insertions of the common tendon, as well as the continuation of that tendon into the patellar tendon, the anterior and posterior and lateral muscles of the leg and their tendinous insertions, and the ligaments and tendons of the ankle and foot ranging in size from small to relatively large (e.g., Archilles tendon).

Particular implementations, according to certain aspects of the present invention, can include repair in connection with the major ligament reconstructions that are being performed on a daily basis in orthopedics/sports medicine disciplines, including treatments of the anterior crociate ligament (ACL), the posterior cruciate ligament (PCL), the medial and lateral collateral ligaments, the medial and lateral meniscus, the rotator cuff and biceps tendon musculature, as well as smaller ligaments such as the medial and lateral collateral ligaments of the elbow, the triangular fibrocartilage complex (TFCC) and other ligaments of the wrist and distal radial ulnar joint, as well as the ankle ligaments including but not limited to the anterior talofibular, calcaneofibular ligament, posterior talofibular ligament, and deltoid ligament.

Included within the scope of the present invention are the additional ligaments that support the spine and the motion segments. The methods of the present invention can thus be applied to, for example, ligaments including the anterior longitudinal ligament, posterior longitudinal ligament, facet joint capsules and capsular ligaments, supraspinous ligament, and intraspinous ligament, which may give rise to additional structural stability to the spine and motion segments that may be involved in conjunction with disk degeneration, pars defects, anterior listhesis or retrolisthesis or laterallisthesis or rotatory scoliosis.

The aforementioned group of applications, including treatments of ligaments related to the joints of the upper and lower limbs, as well as the pelvis, is only a partial list. In one or more of the above contexts, application of a tissue-generating or collagen-promoting implant according to the present invention can provide structural support in the healing of ligaments and tendons, whether the defect, injury or area of interest is at (i) any location of the ligament or adjacent tissues including the origin and insertion thereof, or (ii) any location of the tendon or adjacent tissues such as the musculotendinous junction or anywhere in the tendinous region or at the insertion of the tendon insertion. The scope and field of the present invention for orthopedic tendons and ligament reconstruction, however, is vast and is intended to include any of the major or minor joints with ligaments or tendons that may be injured or otherwise determined to be in need of or likely to benefit from an intervention or treatment using tissue-generating implants.

In accordance with a feature of the present invention, methods are provided for treating ligaments and tendons such as, for example, those set forth above. Tissue-generating implants can be introduced onto and/or into one or more tissues of interest in connection with repairs or treatments of ligaments and tendons in relation to or within an organism. The tissue-generating implants can include particles, such as tissue-growth-inducing particles, such as microparticles which have smooth surfaces that are substantially free from corners and edges and which, for example, are suspended in a biocompatible medium.

The tissue-generating implant can be inserted (e.g., injected) into a ligament or tendon, such as a partial or complete ligament or tendon defect, to thereby facilitate or augment a repair of the ligament or tendon defect. A partial ligament or tendon defect may comprise a ligament or tendon which is not entirely severed. A complete ligament or tendon defect may include for example a ligament which has been completely severed or detached and which, by means known to those skilled in the art, such as, for example, anastomosis using sutures, has been or will be reattached or mended.

Implementations of the present invention can include treatment of patients with, for example, congenital, idiopathic, or acquired scoliosis or kyphosis, by the addition of tissue-generating implants to the region in question which shows the abnormal curvature. The provision of additional structural support to one particular side of a motion segment can favor the mechanics in that region and can provide a means for retarding progression of the curvature or possibly even correcting the curvature.

Generally, in one or more of any of the above applications, the addition of the tissue-generating implant may allow increased structural support and integrity to the repair site (e.g., the motion segment), so as, in the example of spinal applications for example, to attenuate or minimize abnormal movement and/or increase the inherent stability of the spine. Accordingly, representative applications of the tissue-generating implant can include providing structural support to ligaments or tendons that are partially or completely severed, or can include augmenting the repairs. For instance, the tissue-generating implant can provide a biological scaffold helping to support fixation for repair or augmentation of the ligament or tendon in question, and can also operate as a partial permanent connective tissue scaffold in the ligament or tendon repair.

As but one exemplary area of application of the present invention, the tissue-generating implant can be inserted into either the ACL or PCL requiring surgery to thereby assist in the healing. The tissue-generating implant can be used, for example, to strengthen the collateral ligaments in the event that they are torn with a grade 1 or grade 2 tear to thereby potentiate or accelerate the healing, and in some instances obviate the need for, or reduce a necessity or extent of, surgical intervention.

Treatment of ligaments or tendons by insertion of the tissue-generating implants in accordance with the present invention can serve, ultimately, to augment those ligaments or tendons with additional host tissue. The additional host tissue is not implanted but, rather, is generated naturally by the host at the site of the insertion, and integrated into existing tissues by the host at the site of insertion. This natural introduction of host tissue onto or into the ligament or tendon can increase the healing strength of these tissues.

The tissue-generating implant typically is carried (e.g., suspended) in a biocompatible medium, and the treatment typically comprises injection of the tissue-generating implant into a partial or complete ligament or tendon defect or area of interest.

Following insertion (e.g., injection) of the tissue-generating implant into an area or areas of interest of a ligament or tendon, such as an ACL, PCL or one of the medial and collateral ligaments, the tissue-generating implant in accordance with one aspect of the present invention begins to undergo a complete or at least partial biodegradation of the biocompatible medium. In a representative embodiment, the biocompatible medium comprises bovine collagen which, following insertion of the tissue-generating implant, begins to be (i) resorbed into or via tissues of the host mammalian body and/or (ii) replaced or supplemented with host tissue (e.g., collagen). In a representative embodiment, the biocompatible medium is both resorbed and replaced with host tissues. Optionally, in any of the above-stated applications, such as injection of the tissue-generating implant into the collateral ligaments, ligaments, tendons or adjacent tissues, such as the adjacent articular cartilage, can be perforated as outlined below or otherwise treated to enhance a supply of fluid (e.g. blood) to the area of treatment or repair. The additional availability of fluid, in turn, can assist in resorption of the biocompatible medium and/or the replacement or supplementation thereof with host tissue.

In a representative embodiment comprising insertion into a ligament or tendon of a tissue-generating implant comprising microparticles which have smooth surfaces free from corners and edges and which are suspended in a biocompatible medium, the microparticles induce formation of host tissue (e.g., collagen) at or near the region of insertion. In one example, the microparticles comprise polymethylmethacrylate (PMMA) microspheres, and host collagen is formed around these PMMA microspheres maintaining their position. The addition of this host collagen then gives rise to structural support and stability to, for example, the ACL or PCL deficient knee or ACL/PCL partially deficient knee. Certainly in acute injuries in which the ACL or PCL is being repaired, the addition of the present tissue-generating implant can give rise to increased stability and success for the repair. The smaller ligaments in the carpus and the distal radial ulnar joint and the larger ligaments such as the ACL and PCL are amenable to treatment using the tissue-generating implant methods of the present invention, as well.

In the contexts of ligaments and tendons, the tissue-generating implant can be inserted, for example, injected via a syringe needle, to a partial or complete ligament or tendon defect or area of interest and extended along a length of an insertion-device (e.g., needle) path as, for example, the insertion device is withdrawn. For instance, as discussed below, the tissue-generating implant can be injected via a syringe needle to an anastomosis site and extended up to the origin and insertion point of the ligament in question. Tissue treatments, such as microperforations, also discussed below, can be formed the same way, with a needle or awl to insure increased blood flow to the surrounding tissue.

Insertions (e.g., injections) of the tissue-generating implant may be formed in directions parallel to lengths of the ligaments or tendons, along directions perpendicular to lengths of the ligaments or tendons, and/or in any other directions or combinations of directions. The directions and/or lengths of the injections may vary along similar or different paths or axes, and the amounts of tissue-generating implant may vary per unit length along individual injection paths and/or among different injection paths. Such variances of amounts of tissue-generating implant may differ per unit length along individual injections and/or between various injections as a result of varying types of tissue-generating implants and/or biocompatible mediums being used, varying injection rates, varying withdrawal rates, varying diameter injection devices, and other relative variances in injection techniques and materials.

Tissue treatments, such as perforations or, in a representative embodiment, microperforations, may be formed on or within ligaments or tendons to be treated, and/or onto or within adjacent tissues, to facilitate tissue reactions such as, for example, an increase of fluid (e.g., blood) flow to one or more areas of interest. The treatments (e.g., perforations) may be formed in point, straight or curved segments along any direction, orientation, axis or axes with respect to the ligament, tendon and/or adjacent tissue. Perforations may be formed, for example, with a needle or awl in the ligament, tendon and/or adjacent tissue, thus forming, for example, short or elongate fluid-flow paths. In examples involving ligament or tendon anastomosis procedures, proximal and/or distal ends of the ligaments or tendons can be perforated, as described below. The perforations can be formed at the anastomosis site to extend up to the origin and insertion point of the ligament in question. Generally, the tissue treatments (e.g., perforations) as described herein may be formed in directions parallel to lengths of the ligaments or tendons, along directions perpendicular to lengths of the ligaments or tendons, and/or along any directions or combinations of directions therebetween. The directions and/or lengths of the perforations may vary along similar or different paths or axes, and the cross-sectional areas or diameters of the perforations may vary per unit length along individual perforations and/or between perforations, as a result of, for example, varying types, sizes and shapes of perforating instruments being used and varying perforating techniques.

When the tissue-generating implant is inserted according to the present invention into ligaments, such as the smaller ligaments, tissue treatments (e.g., microperforations made with a needle or awl) can be introduced at the origins and insertions of the ligaments to increase blood flow to the surrounding tissues. In addition, or alternatively, when the tissue-generating implant is placed, for example, around and/or near a ligament (especially onto or around an area of injury or damage to the ligament or tendon), tissue treatments (e.g., microperforations) can be introduced at the origin and insertion of the ligament reconstruction to afford increased blood flow to the tissue-generating implant, thus assuring the resorption of the biocompatible medium (e.g., bovine collagen) and replacement with host tissue (e.g., collagen), and increasing a structural support given to the ligament or ligaments in question. With tendons, either percutaneous or open repair can be utilized with the tissue-generating implant at the time of the surgery to augment its structural integrity. As for tendons, blood flow from the musculotendinous junction and tissue treatments (e.g., perforations) at the distal insertion can be sufficient to allow or enhance blood flow to result in suitable biocompatible medium (e.g., bovine collagen) resorption and replacement with host tissue (e.g., human collagen), thereby providing structural support to the tendons as well. In an exemplary embodiment implementing perforations placed at the origin insertion of the ligament or at the insertion of the tendon, the perforations may need only be microperforations to increase the blood flow to that region to ensure that this resorption occurs over an appropriate period of time.

In some implementations the tissue-generating implant can be impregnated with a chromophobe, which can be activated from outside the body with a laser to accelerate a biological reaction within the ligament or tendon.

In accordance with one aspect of the present invention, the tissue-generating implant can be applied to an anastomosis site of a ligament or a tendon in, for example, an open procedure. The tissue-generating implant can be applied in or to at least one of the ligament or tendon (e.g. ligament or tendon ends) at any time prior to, during and/or after the anastomosis. In a representative embodiment, the tissue-generating implant is injected into the ligament or tendon ends prior to anatomical approximation and attachment of the ends together. For example, in a tendon anastomosis procedure, two severed tendon ends can be anatomically approximated while endeavoring to minimize tension and forcep manipulation which can cause scarring. The tissue-generating implant can be injected via a syringe needle to the anastomosis site and extended up to the origin and insertion point(s) of the tendon(s) in question. Optional microperforations as discussed below can be introduced, for example, in the same or a similar way with a needle or awl to increase blood flow to the surrounding tissue. The tendon ends can now be sewn together, using for example, 4-0 Mersilene sutures according to well known surgical manners. Modified Bunnell sutures can be used, wherein the knots are securely tied to avoid tendon end gapping after approximating forces are removed. A running 6-0 nylon peritenon suture can be used, for example, on the anterior half of the tendon repair. The posterior half of the tendon repair can then be made accessible for examining the anatomical accuracy of the repair and/or completing the tendon running suture.

At some point or points prior to, during, or following any treatment (e.g., anastomosis) described herein, at least one exposed surface (e.g., one or more of a proximal end and a distal end of the ligament or tendon) can be perforated or otherwise treated to, for example, increase blood flow to one or more adjacent or surrounding tissues. For example, microperforations can be formed using a needle or awl in the proximal and distal ligament or tendon ends to facilitate increased blood flow to surrounding tissues. In one implementation, microperforations introduced to the anastomosis site extend up to the origin and insertion point of the ligament or tendon in question. As for tendon repair it is readily envisioned by those skilled in the art that tendons go through early or late rupture. During the early phase, rapid loading or stretching of the tendons may lead to failure of the anastomosis site. The late rupture can occur at the same site, but is due to the biologic effects of the cells and blood vessels coming into the repair site.

The tissue-generating implant of the present invention preferably comprises a plurality of microparticles, which can comprise solid microparticles in representative embodiments. In modified implementations, the microparticles may not be altogether solid, such as implementations involving hollow or porous microparticles. As used herein, the term 'microparticles' refers to particles (e.g. in a dust or powder form) possessing an average diameter of 500 microns or less. Typically, the average diameter will be greater than about 20 microns rendering the microparticles too large to be 'eaten' by monocytes. The microparticles can have diameters sufficient to keep them from being washed away through lymph tracts or other tissue tracts from the implantation site. If the microparticles do not have a spherical form, then the diameter as used herein refers to the greatest diameter of the smallest cross sectional area. It is, however, also possible to use smaller microparticles ranging from 5 to 10 microns in diameter. Typically, the microparticles will have an average diameter less than about 200 microns. In representative embodiments, the microparticles can have an average diameter of about 15 to about 200 microns and in certain implementations from about 15 to about 60 microns. In representative configurations, the microparticles are small enough to be injected through a fine gauge cannula or an injection syringe into and/or onto the desired ligament or tendon. Particles having the diameters specified herein may have a relatively minimal effect on the surrounding tissues, i.e., muscle adjacent tendons, bone and articular cartilage.

Due to the formed surface and size of the microparticles used, they are not detected by the endogenous macrophages as foreign bodies so that no defensive reaction takes place. According to a representative embodiment, the microparticles have spherical forms or spherical-like forms capable of forming closely-packed arrangements at the site where they have been implanted and further capable of being individually encapsulated by tissue and material such as collagen The microparticles, which in a representative embodiment may comprise PMMA spherical beads, after being inserted into the ligament or tendon, may be encapsulated by delicate capsules of connective tissue and/or are embedded into connective-tissue tissue or fibers and remain stationary in the tissue. Use of a biocompatible medium as described herein is not mandatory since the microparticles can be inserted (e.g., placed) or injected also without a biocompatible medium into the body.

Once placed into the ligament or tendon, the tissue-generating implant may mimic or provide a substitute for at least one characteristic of the physiologic structure of the ligament or tendon. For example, the tissue-generating implant may mimic and/or operate as a partial artificial part of the ligament or tendon. Accordingly, a morphology of the ligament or tendon may be altered or improved following implantation of the tissue-generating implant. For instance, the accumulation of the microparticles of the tissue-generating implant and/or the accumulation of scar tissue around the microparticles within the ligament or tendon can impart a certain physical bulking or stability to the interior ligament or tendon. Later testing after the tissue-generating implant has matured (e.g., been incorporated into the host tissue through, for example, formation of permanent scar tissue around the microparticles of the implant) can yield an increase in, for example, the strength of the ligament or tendon.

Regarding maturation of the microparticles, which in a representative embodiment may comprise PMMA spherical beads, as a result of the size and physical stability of the PMMA beads, they cannot be phagocytised or lysed. In order to isolate the foreign body, the animal body can only fibrotically wall off the foreign bodies in the form of scar tissue. Such a process takes place with almost any foreign body which cannot be destroyed by the animal body. To the extent present, the fibrotic growth of connective tissue is a natural reaction to the lesion of the tissue caused by the insertion instrument and to the presence of the microparticles. The fibrotic reaction may occur during 3-6 months after injection of the tissue-generating implant due to the smooth and chemically inert surfaces of the microparticles (e.g., PMMA beads). From then on, the beads remain in the tissue without reaction and provide for the formation and existence of permanent fibrovascular connective tissue.

The tissue-generating implant can in one implementation comprise a histocompatible solid in the form of a powder. The microparticles forming the solid may be incorporated into a biocompatible medium and injected, for instance, with an injection needle at the injury site.

It can be advantageous for the microparticles used according to an embodiment of the present invention to have a smooth surface and be free from corners and edges, such that the microparticles don't have sharp transitions on their surfaces. In addition they may not have peaks of any kind or tapered projections. According to one implementation, the surface does not have pores. In another implementation, the surfaces may comprise pores. Although smooth, and especially spherical particles can be advantageous, in some embodiments, microparticles of with corners or peaks or the like may still be used in the present ligament and tendon treatment application.

In many advantageous embodiments, the transition from one outer surface to the other outer surface of the microparticles as used according to one embodiment of the present invention occurs in a continuous manner. If such transitions are present, as is the case for the edges of a cube, such transitions may be smoothed. According to an embodiment of the present invention, microparticles which are crystalline (for instance needle-shaped) or microparticles which have been obtained by mechanically breaking up greater units into small pieces, are not used to the extent the microparticles possess the above-mentioned sharp edges and corners. Due to the smooth surface structure damage to cells and other tissue structures is minimized. In addition, the danger of causing reactions of the tissue, such a foreign body reactions or granulous formation, which may be followed by infections, is minimized.

In one implementation, dynamically balanced microparticles and in particular microparticles having an elliptic or spherical form can be used. In addition, it is possible to use microparticles of a different geometrical form if all, or in another embodiment, a majority, of the microparticles have a smooth and smoothed-off surface. The inert, histocompatible material of the microparticles used according to representative embodiments of the present invention can comprise glass beads or glass pellets having a smooth and/or smoothed off surface. The microparticles used, according to representative implementations of the present invention, can comprise a polymer, and in particular a completely cured and fully polymerized polymer so that no remaining monomers, which may be toxic or may cause cancer, are incorporated into the body of the treated patient. Fully polymerized PMMA is histocompatible and can be incorporated in the human body without harmful toxic or carcinogenic reactions so that it can be considered as chemically and physically inert and biocompatible. For these reasons, PMMA polymers have already been used for manufacturing implants such as for the plastic covering of a bone defect in the face and in the cranium, or as in a total hip or total knee arthroplasty. The polymer is also being used for manufacturing artificial teeth, and for manufacturing intra-articular lenses and dialysis membranes. In principle, it is possible to use any inert histocompatible polymer for producing the microparticles used according to the present invention. Modified embodiments may comprise, in whole or in part, non-polymer microparticles. In an exemplary embodiment, the tissue-generating implant comprises one or more of the implants described under the name Artecoll®. Exemplary embodiments are also described in the U.S. Pat. No. 5,344,452, the entire contents of which is incorporated herein by reference.

The implant material may comprise, for example, about 20% substantially smooth spherical PMMA beads ranging in size from about 32-40 micrometer diameter, and with low levels of methylmethacrylate monomer impurities. The remaining 80% may comprise a solution of partially denatured collagen, which may be about 3.5% collagen in a solution of water and/or alcohol. In one embodiment, there are about 6 million particles per cc of implant material.

To inject the microparticles or polymer microparticles used according to the present invention as a tissue-generating implant for a ligament or tendon, the microparticles can be suspended in a kind of biocompatible medium. A gel which is known per se, and is degraded within the body, for instance, on the basis of gelatin or, preferably, collagen, can be used as a biocompatible medium. The biocompatible medium used according to one implementation of the present invention can comprise a tenside, such as Tween ad, since such a tenside changes the surface tension of water so that the microparticles, and in particular embodiments, the polymer microparticles, have more uniform distribution.

The inserting can comprise inserting a tissue-generating implant into the ligament or tendon while viewing at least a part of the ligament or tendon through a scope. The scope can comprise a video fluoroscope, and the inserting can be fluoroscopically guided. In one implementation, the tissue-generating implant can be impregnated with a water soluble radiopaque dye to facilitate visualization during the inserting of the tissue-generating implant into the ligament or tendon. The radiopaque dye can comprise barium.

The mixing ratio of the components of the biocompatible medium can be chosen according to the needs, and, for example, according to the size of the insertion device used for, or the type of, the insertion. For the application or injection of the tissue-generating implant used according to an embodiment of the present invention, the microparticles can be suspended or slurried in a fluid inert medium.

Additionally, medical kits may be produced containing elements necessary for treating and/or repairing tendons and ligaments with the tissue-promoting implant. Such a kit may include a quantity of the implant, and a delivery device, such as a syringe or other applicator. One or more surgical tools used in conventional tendon and/or ligament repair surgery are also advantageously provided in such kits.

The above-described embodiments have been provided by way of example, and the present invention is not limited to these examples. Multiple variations and modifications to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the present invention is not intended to be limited by the disclosed embodiments.

What is claimed is:

1. A method of treating a ligament comprising
   identifying a defect in the ligament of a patient having congenital, idiopathic, or acquired scoliosis or kyphosis and
   delivering an injectable composition comprising loose polymer microparticles suspended in partially denatured collagen and at least one of water, alcohol, saline, a tenside, radiopaque dye, and a chromophobe onto or into the ligament,
   wherein the ligament is in a region of the patient's spine exhibiting abnormal curvature and is a spinal ligament selected from an anterior longitudinal ligament, a posterior longitudinal ligament, a supraspinous ligament, an intraspinous ligament, and a capsular ligament,
   wherein said composition forms a biological scaffold comprising at least a portion of the microparticles, and wherein the biological scaffold operates as partial connective tissue in the ligament.

2. The method of claim 1, wherein said collagen is configured to be partially replaced with host tissue.

3. The method of claim 1, wherein the microparticles comprise a histocompatible solid.

4. The method of claim 1, wherein said microparticles are substantially spherical with diameters in the range of about 15 to about 200 microns.

5. The method of claim 1, further comprising performing tissue treatments on or within the ligament or adjacent tissue to facilitate tissue reactions.

6. The method of claim 1, further comprising retarding progression of the curvature or partially correcting the curvature.

7. The method of claim 1, wherein the composition comprises a chromophobe, the method further comprising activating the chromophobe with a laser to accelerate a reaction in or near the ligament.

8. The method of claim 1, wherein the composition comprises a radiopaque material, the method further comprising visualizing the composition via the radiopaque material.

9. The method of claim 8, wherein the radiopaque material comprises barium.

10. The method of claim 1, additionally comprising viewing the ligament through a scope.

11. The method of claim 10, wherein the scope comprises a video fluoroscope and delivering the composition is fluoroscopically guided.

* * * * *

UNITED STATES PATENT AND TRADEMARK OFFICE
CERTIFICATE OF CORRECTION

PATENT NO. : 8,127,770 B2  
APPLICATION NO. : 11/215300  
DATED : March 6, 2012  
INVENTOR(S) : Alleyne et al.

Page 1 of 1

It is certified that error appears in the above-identified patent and that said Letters Patent is hereby corrected as shown below:

On Title Page 1 (Item 54) Title, line 2, and column 1, line 2, change "TREAMENT" to --TREATMENT--.

On Title Page 1 (Item 56), under U.S. Patent Documents, add --6,107,466 A 8/2000 Hasan et al.--.

On Title Page 1 (Item 56), line 39, under Other Publications, change "Artecolle®" to --Artecoll®--.

In column 7, line 19, change "repair" to --repair,--.

In column 10, line 34, in Claim 1, change "intraspinous" to --interspinous--.

Signed and Sealed this  
Twenty-fifth Day of September, 2012

David J. Kappos  
*Director of the United States Patent and Trademark Office*